United States Patent
Zhou

(10) Patent No.: US 10,561,709 B2
(45) Date of Patent: Feb. 18, 2020

(54) METHODS AND COMPOSITIONS OF NEUREGULINS FOR PREVENTING, TREATING OR DELAYING PRESERVED EJECTION FRACTION CARDIAC FAILURE

(71) Applicant: Zensun (Shanghai) Science & Technology, Co., Ltd., Shanghai (CN)

(72) Inventor: Mingdong Zhou, Shanghai (CN)

(73) Assignee: Zensun (Shanghai) Science & Technology, Co., Ltd., Shanghai (CN)

( * ) Notice: Subject to any disclaimer, the term of this patent is extended or adjusted under 35 U.S.C. 154(b) by 0 days.

(21) Appl. No.: 15/518,730

(22) PCT Filed: Oct. 8, 2015

(86) PCT No.: PCT/CN2015/091459
§ 371 (c)(1),
(2) Date: Apr. 12, 2017

(87) PCT Pub. No.: WO2016/058493
PCT Pub. Date: Apr. 21, 2016

(65) Prior Publication Data
US 2017/0232068 A1 Aug. 17, 2017

(30) Foreign Application Priority Data
Oct. 17, 2014 (CN) .......................... 2014 1 0550212

(51) Int. Cl.
| | | |
|---|---|---|
| A61K 38/17 | (2006.01) | |
| A61K 38/18 | (2006.01) | |
| C07K 14/475 | (2006.01) | |
| A61K 9/00 | (2006.01) | |
| A61K 9/19 | (2006.01) | |
| A61K 45/06 | (2006.01) | |

(52) U.S. Cl.
CPC ........ *A61K 38/1883* (2013.01); *A61K 9/0019* (2013.01); *A61K 9/19* (2013.01); *A61K 45/06* (2013.01)

(58) Field of Classification Search
None
See application file for complete search history.

(56) References Cited

U.S. PATENT DOCUMENTS

| | | |
|---|---|---|
| 5,530,109 A | 6/1996 | Goodearl et al. |
| 5,716,930 A | 2/1998 | Goodearl et al. |
| 5,834,229 A | 11/1998 | Vandlen et al. |
| 6,054,261 A | 6/2000 | Masterson |
| 6,444,642 B1 | 9/2002 | Sklar et al. |
| 6,635,249 B1 * | 10/2003 | Marchionni ......... A61K 39/395 424/145.1 |
| 6,750,196 B1 | 6/2004 | Reh et al. |
| 7,063,961 B2 | 6/2006 | Ballinger et al. |
| 7,115,554 B1 | 10/2006 | Sklar et al. |
| 7,226,907 B1 | 6/2007 | Zhou |
| 7,612,164 B2 | 11/2009 | Zhou |
| 7,795,212 B2 | 9/2010 | Zhou |
| 7,964,555 B2 | 6/2011 | Zhou |
| 8,476,405 B2 | 7/2013 | Zhou |
| 8,609,620 B2 | 12/2013 | Zhou |
| 8,785,387 B2 | 7/2014 | Zhou |
| 9,012,400 B2 | 4/2015 | Zhou |
| 9,089,524 B2 | 7/2015 | Zhou |
| 9,340,597 B2 | 5/2016 | Zhou |
| 9,434,777 B2 | 9/2016 | Zhou |
| 9,555,076 B2 | 1/2017 | Zhou |
| 9,580,515 B2 | 2/2017 | Zhou |
| 9,655,949 B2 | 5/2017 | Zhou |
| 10,098,834 B2 | 10/2018 | Zhou |
| 10,112,983 B2 | 10/2018 | Zhou |
| 2006/0160062 A1 | 7/2006 | Young |
| 2006/0199767 A1 | 9/2006 | Zhou |
| 2007/0129296 A1 | 6/2007 | Zhou |
| 2007/0141548 A1 | 6/2007 | Kohl et al. |
| 2007/0190127 A1 | 8/2007 | Zhou |
| 2007/0213264 A1 | 9/2007 | Zhou |
| 2009/0156488 A1 | 6/2009 | Zhou |
| 2011/0135595 A1 | 6/2011 | Zhuo |
| 2011/0229444 A1 | 9/2011 | Zhou |

(Continued)

FOREIGN PATENT DOCUMENTS

| | | |
|---|---|---|
| AU | 68278/94 A | 11/1994 |
| CN | 1276381 A | 12/2000 |

(Continued)

OTHER PUBLICATIONS

Britsch et al., "The ErbB2 and ErbB3 receptors sand their ligand, neregulin-1, are essential for development of the sympathetic nervous system," Genes Dev., 12:1825-1836 (1998).
Carraway et al., "Neuregulin-2, a new ligand of ErbB/ErbB4-receptor tyrosine kinase," *Nature*, 387:512-516 (1997).
Chen et al., "Expression and Regulation of Cardiotrophin-1 in Ischemia-1 Reinfusion Cardiac Muscle of Rats and Effect of Neuregulin-1," J Appl Clin Pediatr. 21(1):29-52 (2006). (English Abstract only).
Falls et al. "Neuregulins: functions, forms, and signaling strategies," *Exp. Cell Res.*, 284(1):14-30 (2003).

(Continued)

*Primary Examiner* — Christine J Saoud
*Assistant Examiner* — Jon M Lockard
(74) *Attorney, Agent, or Firm* — Jones Day

(57) ABSTRACT

Disclosed are the use of neuregulin proteins in preparing a medicine for preventing, treating or delaying preserved ejection fraction cardiac failure in mammals, and a method for using the medicine. Also provided in the present invention is a method for preventing, treating or delaying preserved ejection fraction cardiac failure in mammals, comprising using the medication containing the neuregulin proteins in a special population having the disease or being at risk of having the disease.

4 Claims, No Drawings
Specification includes a Sequence Listing.

(56) References Cited

U.S. PATENT DOCUMENTS

| | | | |
|---|---|---|---|
| 2013/0078235 | A1 | 3/2013 | Zhou |
| 2013/0196911 | A1 | 8/2013 | Jay et al. |
| 2013/0259924 | A1 | 10/2013 | Bancel et al. |
| 2014/0364366 | A1 | 12/2014 | Zhou |
| 2015/0284440 | A1 | 10/2015 | Zhou |
| 2016/0095903 | A1 | 4/2016 | Zhou |
| 2016/0324876 | A1 | 11/2016 | Zhou |
| 2017/0007671 | A1 | 1/2017 | Zhou |
| 2017/0189489 | A1 | 7/2017 | Zhou |
| 2017/0313784 | A1 | 11/2017 | Zhou |
| 2017/0326204 | A1 | 11/2017 | Zhou |
| 2017/0360889 | A1 | 12/2017 | Zhou |
| 2017/0368140 | A1 | 12/2017 | Zhou |
| 2018/0104311 | A1 | 4/2018 | Zhou |
| 2019/0240145 | A1 | 8/2019 | Zhou |

FOREIGN PATENT DOCUMENTS

| | | | |
|---|---|---|---|
| CN | | 1138785 C | 2/2004 |
| CN | | 1498656 A | 5/2004 |
| CN | | 1715926 A | 1/2006 |
| CN | | 1768859 A | 5/2006 |
| CN | | 1836731 A | 9/2006 |
| CN | | 101310766 A | 11/2008 |
| CN | | 101310779 A | 11/2008 |
| CN | | 101394861 A | 3/2009 |
| CN | | 102159236 A | 8/2011 |
| RU | | 2180843 C2 | 3/2002 |
| WO | WO 1989/01489 A | | 2/1989 |
| WO | WO 1994/26298 A1 | | 11/1994 |
| WO | WO 1997/09425 A1 | | 3/1997 |
| WO | WO 1999/18976 A1 | | 4/1999 |
| WO | WO 2000/37095 A1 | | 6/2000 |
| WO | WO 2000/64400 A2 | | 11/2000 |
| WO | WO 2000/78347 A1 | | 12/2000 |
| WO | WO 2001/64877 A2 | | 9/2001 |
| WO | WO 2001/89568 A1 | | 11/2001 |
| WO | WO 2002/024889 A2 | | 3/2002 |
| WO | WO 2002/040683 A2 | | 5/2002 |
| WO | WO 2003/099300 A1 | | 12/2003 |
| WO | WO 2003/099320 A1 | | 12/2003 |
| WO | WO 2003/099321 A1 | | 12/2003 |
| WO | WO 2004/050894 A2 | | 6/2004 |
| WO | WO 2004/112763 A2 | | 12/2004 |
| WO | WO 2006/108208 A1 | | 10/2006 |
| WO | WO 2007/062594 A1 | | 6/2007 |
| WO | WO 2007/076701 A1 | | 7/2007 |
| WO | WO 2008/028405 A1 | | 3/2008 |
| WO | WO 2008/089994 A1 | | 7/2008 |
| WO | WO 2009/033373 A1 | | 3/2009 |
| WO | WO 2010/060265 A1 | | 6/2010 |
| WO | WO 2010/060266 A1 | | 6/2010 |
| WO | WO 2010/142141 A1 | | 12/2010 |
| WO | WO 2011/091723 A1 | | 8/2011 |
| WO | WO 2011/112864 A1 | | 9/2011 |
| WO | WO 2012/012682 A2 | | 1/2012 |
| WO | WO 2013/053076 A1 | | 4/2013 |
| WO | WO 2013/053158 A1 | | 4/2013 |
| WO | WO 2013/053201 A1 | | 4/2013 |
| WO | WO 2014/056121 A1 | | 4/2014 |
| WO | WO 2014/138502 A1 | | 9/2014 |
| WO | WO 2014/187342 A1 | | 11/2014 |
| WO | WO 2015/101182 A1 | | 7/2015 |
| WO | WO 2015/101208 A1 | | 7/2015 |
| WO | WO 2016/045493 A1 | | 3/2016 |

OTHER PUBLICATIONS

Genbank Accession No. AJ247087, Apr. 15, 2005.
Genbank Accession No. NM_001110810, Nov. 24, 2007.
Higashiyama et al., "A novel brain-derived member of the epidermal growth factor family that interacts with ErbB3 and EibB4," *J. Biochem.*, 122:675-680 (1997).
Hijazi et al., "NRG-3 in human breast cancers: activation of multiple erbB family proteins," *Int. J. Oncol.*, 13:1061-1067 (1998).
Jones et al., "Binding interaction of the heregulinbeta egf domain with ErbB3 and ErbB4 receptors assessed by alanine scanning mutagenesis," *J. Biol. Chem.*,273(19):11667-11674 (1998).
Kuramochi et al., "Cardiac endothelial cells regulate reactive oxygen species-induced cardiomyocyte apoptosis through neuregulin-1β/erbB4 signaling," *J. Biol. Chem.*, 279(49):51141-51147 (2004).
Liu, "Protective effects of neuregulin-1β on chronic contractibility cardiac failure and correlative mechanisms research," Chinese Master's Thesis Full-text database, Medicine and Health Sciences, Jun. 2010, English abstract attached.
Luo et al., "Computational analysis of molecular basis of 1:1 interactions of NRG-lbeta wild-type and variants with ErbB3 and ErbB4," *Proteins*, 59(4):742-756 (2005).
Massova et al., "Computational alanine scanning to probe protein-protein interactions: a novel approach to evaluate binding fee energies," *J. Am. Chem. Soc.*, 121(36):8133-8143 (1999).
Ngo et al., "Computational complexity, protein structure prediction, and the Levinthal paradox," In Merz and Le Grand (Eds.), *The Protein Folding Problem and Tertiary Structure Prediction.* Birkhauser:Boston, pp. 491-495 (1994).
Wang et al., "Improvement of cardiac function and reversal of gap junction remodeling by Neuregulin-1β in volume-overloaded rats with heart failure," *J. Geriatr. Cardiol.*, 9(2):172-179 (2012).
Watson et al., *Molecular Biology of the Gene*, 4th Edition, The Bejacmin/Cummings Publishing Company, Inc., Menlo Park, CA, p. 224 (1987).
Wells, "Additivity of mutational effects in proteins," *Biochem.*, 29(37):8509-8517 (1990).
Yarden et al., "Untangling the ErbB signaling network," *Nat. Rev. Mol. Cell Biol.*, 2(2):127-137 (2001).
Bakalets, "Chronic heart deficiency with preserved left ventricle ejection fraction," Problems of Health and Ecology, Gomel State Medical University, 3(33):7-11 (2012) (English abstract).
Balligand et al., Cardiac endothelium and tissue growth, *Prog. Cardiovasc. Dis.*, 39(4):351-360 (1997).
Chang et al., "Ligands for ErbB-family receptors encoded by a neuregulin-like gene," *Nature*, 387:509-512 (1997).
Chien et al., "Regulation of cardiac gene expression during myocardial growth and hypertrophy: molecular studies of an adaptive physiologic response," *FASEB J.*, Dec. 1991; 5(15):3037-3046.
Chien, "Molecular advances in cardiovascular biology," *Science*, 260(5110):916-917 (1993).
Colucci et al., "Pathphysiology of heart failure," Chapter 13 in *Heart Diseases: A textbook of cardiovascular medicine*, Braunwald, ed., Saunders, Philadelphia. 1996; 5:394-420.
Crone et al., "ErbB2 is essential in the prevention of dilated cardiomyopathy," *Nat Med.*, 8(5):459-465 (2002).
Dias et al., "The molecular basis of skeletal muscle differentiation," *Semin Diagn Pathol.*, Feb. 1994; 11(1):3-14.
Eppstein et al., "Biological activity of liposome-encapsulated murine interferon gamma is mediated by a cell membrane receptor," *Proc. Natl. Acad. Sci. U S A.*, Jun. 1985; 82(11):3688-3692.
Floriniet al., "Stimulation of myogenic differentiation by a neuregulin, glial growth factor 2," *J. Biol. Chem.*, 271(22):12699-12702 (1996).
Galindo et al., "Anti-remodeling and anti-fibrotic effects of the neuregulin-1β glial growth factor 2 in a large animal model of heart failure," *J. Am. Heart Assoc.*,3(5):e000773 (2014).
Gao et al., "A Phase II, randomized, double-blind, multicenter, based on standard therapy, placebo-controlled study of the efficacy and safety of recombinant human neuregulin-1 in patients with chronic heart failure," *J. Am. Coll. Cardiol.*, 55(18):1907-1914 (2010).
Gu et al., "Cardiac functional improvement in rats with myocardial infarction by up-regulating cardiac myosin light chain kinase with neuregulin," *Cardiovasc. Res.*, 88(2):334-343 (2010).
Hein et al., "Altered expression of titin and contractile proteins in failing human myocardium," J. Mol. Cell Cardiol., 26(10):1291-1306 (1994).
Holmes et al., "Identification of heregulin, a specific activator of p185erbB2," Science, 256:1205-1210 (1992).
Hwang et al., "Hepatic uptake and degradation of unilamellar sphingomyelin/cholesterol liposomes: a kinetic study," Proc. Natl. Acad. Sci. U S A., Jul. 1980; 77(7):4030-4034.

(56) References Cited

OTHER PUBLICATIONS

Izumo et al., "Calcineurin—the missing link in cardiac hypertrophy," Nat. Med., 4(6):661-662 (1998).

Langer et al., "Biocompatibility of polymeric delivery systems for macromolecules," J. Biomed. Mater. Res., Mar. 1981; 15(2):267-277.

Liu et al., "Effects of neuregulin on Rhesus monkey heart failure induced by rapid pacing," Sichuan Da Xue Xue Bao Yi Xue Ban, 2009, 40(1):93-96 (English Abstract).

Liu et al., "Neuregulin-1/ErbB-activation improves cardiac function and survival in models of ischemic, dilated, and viral cardiomyopathy," J. Am. Coll. Cardiol., 2006, 48(7):1438-1447.

Mahmood et al., "Selection of the first-time dose in humans: comparison of different approacheds based on interspecies scaling of clearance," J. Clin. Pharm., 43:692-697 (2003).

Olson et al., "Regulation of muscle transcription by the MyoD family. The heart of the matter," Circ. Res., 72(1):1-6 (1993).

Parker et al., "p53-independent expression of p21Cip1 in muscle and other terminally differentiating cells," Science, 267(5200):1024-1027 (1995).

Physicians' Desk Reference. Medical Economics Data Production Co., Montvale, NJ. 1994; pp. 2314-2320.

Rumyantsev, "Interrelations of the proliferation and differentiation processes during cardiac myogenesis and regeneration," Int. Rev. Cytol., 51:186-273 (1977).

Sawyer et al., "Modulation of anthracycline-induced myofibrillar disarray in rat ventricular myocytes by neuregulin-1beta and anti-erbB2: potential mechanism for trastuzumab-induced cardiotoxicity," Circulation, 105(13):1551-1554 (2002).

Schaper et al., "Impairment of the myocardial ultrastructure and changes of the cytoskeleton in dilated cardiomyopathy," Circulation, 83(2):504-514 (1991).

Sidman et al., "Controlled release of macromolecules and pharmaceuticals from synthetic polypeptides based on glutamic acid," Biopolymers, Jan. 1983; 22(1):547-556.

Simpson et al., "Myocyte hypertrophy in neonatal rat heart cultures and its regulation by serum and by catecholamines," Circ. Res. 51(6):787-801 (1982).

Slamon et al., "Use of chemotherapy plus a monoclonal antibody against HER2 for metastatic breast cancer that overexpresses HER2," N. Engl. J. Med., 344(11):783-792 (2001).

Stevenson et al., "Optimizing therapy for complex or refractory heart failure: a management algorithm," Am. Heart J.,135(6 Pt 2 Su):S293-S309 (1998).

Swynghedauw, "Molecular mechanisms of myocardial remodeling," Physiol. Rev., 79(1):215-262 (1999).

U.S. Department of Health and Human Services, Food and Drug Administration, Center for Drug Evaluation and Research (CDER), "Guidance for Industry, estimating the maximum safe starting dose in initial clinical trials for therapeutics in adult heathy volunteers," Jul. 2005.

Zhao et al., "Selective disruption of neuregulin-1 function in vertebrate embryos using ribozyme-tRNA transgenes," Development, 125(10):1899-1907 (1998).

Zhao et al., "Neuregulins promote survival and growth of cardiac myocytes. Persistence of ErbB2 and EibB4 expression in neonatal and adult ventricular myocytes," J. Biol. Chem., 273(17):10261-10269 (1998).

Zhou et al., "Retinoid-dependent pathways suppress myocardial cell hypertrophy," Proc. Natl. Acad. Sci. U S A., 92(16):7391-7395 (1995).

* cited by examiner

SEQUENCE LISTING

<160> NUMBER OF SEQ ID NOS: 1

<210> SEQ ID NO 1
<211> LENGTH: 61
<212> TYPE: PRT
<213> ORGANISM: homo sapiens

<400> SEQUENCE: 1

Ser His Leu Val Lys Cys Ala Glu Lys Glu Lys Thr Phe Cys Val Asn

-continued

```
1               5                   10                  15
Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60
```

METHODS AND COMPOSITIONS OF NEUREGULINS FOR PREVENTING, TREATING OR DELAYING PRESERVED EJECTION FRACTION CARDIAC FAILURE

This application is a U.S. National Stage of International Application No. PCT/CN2015/091459, filed Oct. 8, 2015, which claims priority to Chinese application No. 201410550212.7, filed Oct. 17, 2014, each of which is incorporated herein by reference in their entirety.

This application incorporates by reference a Sequence Listing with this application as an ASCII text file entitled "11748-074-999_Sequence_listing.txt" created on Mar. 22, 2017, and having a size of 850 bytes.

FIELD OF THE INVENTION

The present invention relates to the use of neuregulin protein in the preparation of medicament for preventing, treating or delaying heart failure with preserved ejection fraction in a mammal and methods of using said medicament for preventing, treating or delaying heart failure with preserved ejection fraction in a mammal. Particularly, the present invention provides methods for preventing, treating or delaying heart failure with preserved ejection fraction in a mammal, comprising administering the medicament containing the neuregulin proteins to a special population having or being at risk of having heart failure with preserved ejection fraction. Specially, this invention relates to a new indication of neuregulin in treatment of cardiovascular disease, i.e., heart failure with preserved ejection fraction.

BACKGROUND OF THE INVENTION

Neuregulin (NRG; heregulin, HRG), also known as glial growth factor (GGF) and new differentiation factor (NDF), is a kind of glycoprotein with a molecular weight of 44 KD. As the ligand of tyrosine kinase receptor of ErbB family, neuregulin is responsible for cell signaling. NRGs family has four members: NRG1, NRG2, NRG3 and NRG4 (Falls et al., Exp Cell Res.284:14-30,2003). NRG1 plays an important role in nervous system, heart and breast. It is also evidenced that NRG1 signal transmission plays a part in the development and function of other organ systems, as well as in the pathogenesis of human disease (including schizophrenia and breast cancer). NRG1 has many isomers. The research in gene mutated mice (gene knock-out mice) indicates that isomers with different N terminal region or EGF-like domain have different in vivo functions. The present invention is based on NRG-1β.

NRG-1β is a transmembrane protein (Holmes et al., Science 256, 1205-1210,1992). The extracellular region is N terminal region, comprising immune globulin like domain (Ig-like domain) and EGF-like domain. The intracellular region is C terminal region. Under the action of extracellular matrix metalloproteinase, the extracellular region of NRG is in a free state after being cut off by enzyme, thus facilitate binding to ErbB3 receptor on the cell surface and activating relevant cell signal transmission.

EGF receptor family can be divided into four classes, including ErbB1, ErbB2, ErbB3 and ErbB4, all of which are transmembrane proteins with a molecular weight of around 180-185 KD. They all comprise an extracellular ligand-binding domain in N terminal region except ErbB2. They all have protein tyrosine kinase activity in intracellular C terminal region except ErbB3. ErbB1 is epidermal growth factor receptor while ErbB3 and ErbB4 are neuregulin receptors. Among these neuregulin receptors, only ErbB2 and ErbB4 are highly expressed in heart (Yarden et al., Nat Rev Mol Cell Biol, 2: 127-137,2001).

After NRG binds to the extracellular domain of ErbB3 or ErbB4, it induces the formation of heterodimers of ErbB3, ErbB4 with other ErbB receptors (normally including ErbB2) or homodimers of ErbB4, which results in phosphorylation of the receptor's intracellular region (Yarden et al., Nat Rev Mol Cell Biol, 2: 127-137,2001). The phosphorylated intracellular domain then binds signaling proteins inside the cell, thus activating the downstream AKT or ERK signaling pathway, and inducing a series of cell reactions, such as stimulation or depression of cell proliferation, cell apoptosis, cell migration, cell differentiation or cell adhesion.

NRG plays an particularly important role in the development of heart (WO0037095, CN1276381, WO03099300, WO9426298, U.S. Pat. No. 6,444,642, WO9918976, WO0064400, Zhao et al., J. Biol. Chem. 273, 10261-10269, 1998). At the early stage of embryo development, the expression of NRG is limited in endocardium, whereafter it is released to periphery myocardial cell by paracrine and binds to the extracellular domain of protein tyrosine kinase receptors ErbB4 on cytomembrane, the ErbB4 than forms a heterodimer with ErbB2. The formation and activation of the ErbB4/ErbB2 complex is essential to form the trabecular of sponge-like heart at early phase. The absence of any of the three protein genes for NRG proteins, ErbB4 and ErbB2, would lead to an embryo without trabecular and death in uterus at early development. WO0037095 shows that a certain concentration of neuregulin could sustainably activate ERK signaling pathway, promote the differentiation and growth of myocardial cells, guide the reconstruction of sarcomere and cytoskeleton at the site where myocardial cells are adhered to cells, improve the structure of myocardial cells and enhance myocardial cell contraction. WO0037095 and WO003099300 also indicate that NRG could be used in the detection, diagnosis and treatment of various cardiovascular diseases.

The following is a list of some prior art technical literature related to the present invention: 1. Cardiac muscle function and manipulation:WO0037095; 2. New application of neuregulin and its analogs: CN1276381; 3. Neuregulin based methods and composition for treating cardiovascular diseases: WO03099300; 4. Zhao Y Y, Sawyer D R, Baliga R R, Opel D J, Han X, Marchionni M A and Kelly R A. Neuregulins Promote Survival and Growth of Cardiac Myocytes. J. Biol. Chem. 273, 10261-10269 (1998); 5. Methods for treating muscle diseases and disorder: WO9426298; 6. Methods of increasing myotube formation or survival or muscle cell mitogenesis, differentiation or survival using a neuregulin: U.S. Pat. No. 6,444,642. 7. Therapeutic methods comprising use of a neuregulin: WO9918976; 8. Methods for treating congestive heart failure: WO0064400; 9. Holmes W E, Sliwkowski M X, Akita R W, Henzel W J, Lee J, Park J W, Yansura D, Abadi N, Raab H, Lewis G D, et al. Identification of heregulin, a specific activator p185erbB2. Science 256, 1205-1210 (1992); 10. Falls D L. Neuregulins: functions, forms and signaling strategies. Experimental Cell Research, 284, 14-30 (2003). 11. Yarden Y, Sliwkowski X. Untangling the ErbB signaling Network. Nature Reviews: Molecular Cell Biology, 2127-137 (2001).

Heart failure (HF) is a cardiac insufficiency syndrome caused by various heart diseases, including systolic heart failure (SHF) and diastolic heart failure (DHF). In 2008, the European Society of Cardiology (ESC) issued the *Diagnosis and treatment guidelines of acute/chronic heart failure*, and defined DHF as heart failure with preserved ejection fraction (HF-PEF). Systolic heart failure is a condition in which the heart with decreased myocardium contractility leads to cardiac output that cannot meet the needs of metabolism, tissue or organ hypo perfusion, pulmonary circulation and/or systemic circulation congestion. Heart failure with preserved ejection fraction (HF-PEF) often refers to diastolic heart failure due to the impaired diastolic relaxation of left ventricular and decreased myocardial compliance, myocardial cell hypertrophy and interstitial fibrosis of the left ventricular stiffness increases, which result in impaired diastolic filling, decreased stroke volume, increased left ventricular end diastolic pressure and the occurrence of heart failure. Epidemiological data from the American Heart and Lung Institute in 2006 showed that heart failure with preserved ejection fraction or diastolic heart failure accounted for more than 50% of the total number of patients with heart failure. Heart failure with preserved ejection fraction may exist alone, and also appear with systolic dysfunction. Heart failure with preserved ejection fraction is more common in elderly women with hypertension, diabetes mellitus and left ventricular hypertrophy.

Diastolic heart failure and systolic heart failure have similar symptoms and signs. Patients are usually with high blood pressure and other basic diseases. In the early stage of heart failure, unexplained fatigue, decreased exercise tolerance, heart rate increased 15 to 20 times per minute, may be an early sign of left ventricular function decrease. Then there may be the symptom of exertional dyspnea and paroxysmal nocturnal dyspnea, high pillow sleep. Abdominal or leg edema may occur in patients as the primary or sole symptom, while impaired exercise tolerance in patients occurs gradually.

Diastole is a more complex physiological process involving multiple factors than systole. Therefore, the diagnosis of heart failure with preserved ejection fraction or diastolic heart failure is more difficult than systolic heart failure. When the following conditions are met, the diagnosis can be made:
1. Typical symptoms and signs of heart failure;
2. Normal LVEF (or slightly decrease≥45%), normal left ventricular morphology;
3. There is evidence of underlying heart disease, for example, patients with hypertension have the evidence of left ventricular hypertrophy, left atrial enlargement, and left ventricular diastolic dysfunction in echocardiography;
4. Increased BNP/NT-ProBNP;
5. Echocardiography showed no valvular heart disease, and pericardial disease, hypertrophic cardiomyopathy, restrictive (infiltrative) cardiomyopathy etc. were excluded.

Heart failure with preserved ejection fraction or diastolic heart failure is associated with a variety of causes, in which the left ventricular pressure/volume mechanism is a more recognized pathogenesis. Patients with hypertension, hypertrophic cardiomyopathy, aortic stenosis have significantly increased ventricular end-diastolic pressure, and significantly reduced left ventricular capacity, which affect the ventricular filling, leading to the pressure and capacity curve left shift and the formation of centripetal remodeling. Long-term stress overload causes the occurrence of diastolic heart failure.

Ventricular diastolic function includes two phases, namely relaxation (initiative energy consumption process) and compliance of ventricular muscle. Relaxation of ventricular muscle is the change of heart cavity pressure per unit time during diastole, which is an initiative energy consumption process. Compliance of ventricular muscle is the change of heart cavity pressure caused by the change of unit volume during diastole, which is a passive filling process. Relaxation is the initiative diastolic of ventricular muscle at early diastole, the ability of the cardiac muscle fiber to recover to presystolic length and pressure, and is an energy dependent $Ca^{2+}$ transport initiative energy consumption process, including the isovolumic relaxation and early diastolic rapid filling phase. The left ventricular relaxation is reflected by parameters including isovolumic relaxation (IVRT) duration, the maximum rate of pressure drop (−dp/dt), mitral E peak deceleration time (DT), etc. These parameters obtained by two-dimensional echocardiography and hemodynamic tests could be used to evaluate diastolic function of heart to a certain extent.

In addition, there is no specific treatment for heart failure with preserved ejection fraction. Present therapeutic guidelines include the use of standard therapeutic drugs for controlling blood pressure, reducing ventricular rate, reducing fluid retention (such as angiotensin-converting enzyme inhibitors/angiotensin II receptor inhibitors, β blockers and diuretics) which may improve systolic heart failure symptoms, /,but cannot improve the clinical symptoms and prognosis of heart failure with preserved ejection fraction. Finally, patients with heart failure with preserved ejection fraction or diastolic heart failure have a poor prognosis, a relatively high rate of re-hospitalization and repeated hospitalization, which increase the burden of the entire healthcare system. Systolic heart failure is the outcome of the development of diastolic heart failure. How to improve cardiac diastolic performance in the early stage of diastolic heart failure and prevent it from further deterioration, remains a great challenge in the treatment of diastolic heart failure.

There are no reports on the role of the neuregulin proteins related to heart failure with preserved ejection fraction or diastolic heart failure in the prior art technical literature. The present invention find administration of neuregulin to a mammal can significantly improve the symptoms of heart failure with preserved ejection fraction, and neuregulin can be used for preparing drugs for preventing, treating or delaying heart failure with preserved ejection fraction in a mammal.

THE CONTENT OF THE INVENTION

A. Summary of the Invention

The present invention is based on the scientific discovery that NRG is crucial to the cardiac development, as well as maintenance of function of adult heart. The present invention is based on the scientific discovery that NRG can strengthen the formation of myocardial cell sarcomere, cytoskeleton and intercellular junction. The present invention is also based on the scientific discovery that NRG can improve the heart function of animals or patients with heart failure in animal models and clinical trials. Neuregulin, neuregulin polypeptide, neuregulin derivatives, or compounds which mimic the activities of neuregulins all fall within the scope of the present invention.

The NRG proteins can bind to the ErbB receptor on the surface of myocardial cells, continuously activate the ERK signal pathway in the cell, and change the structure of the myocardial cells, thereby improving the function of myocardial cells.

In a first aspect of the present invention, a method is provided for preventing, treating or delaying heart failure with preserved ejection fraction in a mammal especially human, comprising administering an effective amount of NRG or its functional fragment, or nucleic acid encoding NRG or its functional fragment, or substance improving the yield of NRG and/or functional to the mammal especially human who need or hope to prevent, treat or delay heart failure with preserved ejection fraction, so as to achieve the effect of preventing, treating or delaying heart failure with preserved ejection fraction.

In a second aspect, the present invention provides a pharmaceutical preparation for preventing, treating or delaying heart failure with preserved ejection fraction in a mammal especially human, which comprises an effective amount of NRG or its functional fragment, or nucleic acid encoding NRG or its functional fragment, or substance improving the yield of NRG and/or function and pharmaceutically acceptable carriers, excipients etc. The pharmaceutical preparation may be used in combination with other drug(s) for preventing, treating, or delaying heart failure with preserved ejection fraction.

In another aspect, the present invention provides a composition for preventing, treating or delaying heart failure with preserved ejection fraction in a mammal especially human, which comprises pharmaceutical preparation for preventing, treating or delaying heart failure with preserved ejection fraction in a mammal provided by this invention, and other drug(s) for preventing, treating or delaying heart failure with preserved ejection fraction.

The present invention further provides a kit for preventing, treating or delaying heart failure with preserved ejection fraction in a mammal especially human in a mammal especially human, which comprises one or more doses of pharmaceutical preparation or composition used for preventing, treating or delaying heart failure with preserved ejection fraction, and instructions on how to use the pharmaceutical preparation or composition.

B. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" mean "at least one" or "one or more" unless the context clearly dictates otherwise.

As used herein, "neuregulin" or "NRG" refers to proteins or peptides that can bind and activate ErbB2, ErbB3, ErbB4 or heterodimers or homodimers thereof, including neuregulin isoforms, neuregulin EGF-like domain, polypeptides comprising neuregulin EGF-like domain, neuregulin mutants or derivatives, and any kind of neuregulin-like gene products that can activate the above receptors Neuregulin also includes NRG-1, NRG-2, NRG-3 and NRG-4 proteins, peptides, fragments and compounds that have the functions of neuregulin. In preferred embodiments, neuregulin is a protein or peptide that can bind to and activate ErbB2/ErbB4 or ErbB2/ErbB3 heterodimers, for example, but not for the purpose of restriction, peptides of the present invention includes a fragment of the NRG-1 β2 isoform, i.e., the 177-237 amino acid fragment, which contains the EGF-like domain having the following amino acid sequence: SHLVK-CAEKEKTFCVNGGECFMVKDLSNPSRYLCKCPNEFT-GDRCQNYVMASFYKAEELYQ (SEQ ID NO:1). The NRG proteins of the present invention can activate the receptors above and regulate their biological functions, for example, stimulate the synthesis of acetylcholine receptors in skeletal muscle cells, promote the differentiation and survival of cardiomyocytes and DNA synthesis. The NRG proteins also comprise NRG mutant that possess conservative mutation having no substantially affect on biological function. It is well known to those of skill in this art that mutation of single amino acid in non-critical region generally would not alter the biological activity of the resulting protein or polypeptide (see, e.g., Watson et al., Molecular Biology of the Gene, 4th Edition, 1987, The Bejacmin/Cummings Pub.co.,p. 224). The NRG proteins of the invention can be isolated from natural sources, or obtained through recombination technology, artificial synthesis or other means.

As used herein, "epidermal growth factor-like domain" or "EGF-like domain" refers to a polypeptide fragment encoded by the neuregulin gene that binds to and activates ErbB2, ErbB3, ErbB4, or heterodimers or homodimers thereof, and structurally similar to the EGF receptor binding region as described in WO 00/64400, Holmes et al., Science, 256:1205-1210 (1992); U.S. Pat. Nos. 5,530,109 and 5,716, 930; Hijazi et al., Int. J. Oncol., 13:1061-1067 (1998); Chang et al., Nature, 387:509-512 (1997); Carraway et al., Nature, 387:512-516 (1997); Higashiyama et al., J. Biochem., 122:675-680 (1997); and WO 97/09425, the contents of which are all incorporated herein by reference. In certain embodiments, EGF-like domain binds to and activates ErbB2/ErbB4 or ErbB2/ErbB3 heterodimers. In certain embodiments, EGF-like domain comprises the amino acid sequence of the receptor binding domain of NRG-1. In some embodiments, EGF-like domain refers to amino acid residues 177-226, 177-237, or 177-240 of NRG-1. In certain embodiments, EGF-like domain comprises the amino acid sequence of the receptor binding domain of NRG-2. In certain embodiments, EGF-like domain comprises the amino acid sequence of the receptor binding domain of NRG-3. In certain embodiments, EGF-like domain comprises the amino acid sequence of the receptor binding domain of NRG-4. In certain embodiments, EGF-like domain comprises the amino acid sequence of Ala Glu Lys Glu Lys Thr Phe Cys Val Asn Gly Gly Glu Cys Phe Met Val Lys Asp Leu Ser Asn Pro, as described in U.S. Pat. No. 5,834,229.

As used herein, "heart failure with preserved ejection fraction (HF-PEF)", also known as heart failure with normal left ventricular ejection fraction (HFNEF), heart failure with preserved left ventricular ejection fraction (HF-PLVEF), heart failure with preserved systolic function (HF-PSF), diastolic heart failure (DHF), refers to normal or slightly decreased left ventricular ejection fraction (LVEF), mainly due to impaired left ventricular diastolic relaxation and decreased myocardial compliance, increased stiffness caused by myocardial cell hypertrophy and interstitial fibrosis, resulting in impaired left ventricular diastolic filling, decreased stroke volume, increased left ventricular end diastolic pressure and the occurrence of heart failure. It can exist alone, or appear at the same time with contraction dysfunction.

As used herein, "isovolumic relaxation period (IVRT)" means that when the ventricle is in a isovolumic closed state of pressure drop, the ventricle begins to relax, while the aortic and atrioventricular valves are in the closed state. When left ventricular relaxation is impaired, IVRT prolongs. When left ventricular relaxation improved, IVRT decreases.

As used herein, "pressure drop rate (−dp/dt)" refers to the rate of left ventricular pressure drop during isovolumetric relaxation period. The greater the value, the faster the rate of left ventricular pressure drop, the better the diastolic function. It is one of the reliable indexes to evaluate myocardial relaxation.

As used herein, "mitral E peak" refers to the early diastolic peak (E) of heart mitral valve orifiee, which reflects the maximum blood flow velocity through valve orifiee at left ventricular rapid filling period. The E peak of mitral valve orifiee blood flow curve represents the early diastolic active relaxation of left ventricle and reflects the left ventricular relaxation.

As used herein, "E peak drop time (DT)" refers to the deceleration time of the mitral E peak drop, in other word, the blood flow deceleration caused by early diastolic mitral valve movement to the left atrium, reflects the pressure changes of left atrium in the period of rapid filling. The smaller the value, the more quickly the pressure changes. The decrease of active relaxation usually occurs in the early stage of the disease, which is manifested as the decrease of the early diastolic filling volume of the left ventricle, the decrease of E peak and the prolongation of DT by >240 ms.

As used herein, "Other drug(s) for treatment of heart failure with preserved ejection fraction" refer to the known drugs for treatment of heart failure with preserved ejection fraction, including angiotensin converting enzyme inhibitors/angiotensin II receptor inhibitors, beta receptor antagonists, calcium antagonists, cyclic adenosine monophosphate, catecholamines, nitrates phosphatase inhibitors, diuretics, renin angiotensin aldosterone system (RAS) antagonists, myocardial energy optimization agents etc.

EXAMPLES

Example 1

Study of the Effect of Recombinant Human Neuregulin on Cardiac Function of Hypertensive Heart Failure Rats The study is on the therapeutic effect of recombinant human neuregulin (rhNRG) in SHR hypertensive rats with heart failure. Methods: SHR hypertensive rat strains, normal feeding, monitoring changes of cardiac function during feeding. 16 months later, ejection fraction (EF) decreased to 70%, suggesting that hypertension rat model of heart failure was successfully established. Hypertensive heart failure rats were randomly divided into negative control group, NRG treatment group and captopril treatment group. rhNRG was administered continuously for 5 days, withdrawing for 2 days in a treatment cycle, NRG group received 3 treatment cycles. At the end of the second and third treatment cycle, each group of rats was examined by echocardiography to determine the cardiac function changes. After the third treatment cycle, hemodynamics of the rats were detected.

1. Experimental animals
   1.1 Strain, origin: SHR hypertensive rats strain was bought from the Animal Center of Chinese Academy of Sciences. WKY strain, as the control of SHR, was also bought from the Animal center of Chinese Academy of Sciences.
   1.2 Gender, weeks of age: male, 6 weeks old.
   1.3 Feeding: ordinary rodents feed, free to drink water, 12 hours light-dark cycle 2. Trial drugs
   Specification: Neucardin™, 61 amino acids, produced by Shanghai Zensun Sci & Tech Co., Ltd.
3. Trial materials
   3.1 Cardiac ultrasound diagnostic instrument: Philips Sonos 5500
   3.2 Captopril: Sino American Shanghai Squibb Pharmaceutical Ltd.
4. Experimental methods
   4.1 Establishment of rat model of hypertensive heart failure
   The SHR hypertensive rat strains, normal feeding, and monitoring the cardiac function changes during the feeding. 16 months later, the ejection fraction (EF) of SHR rats decreased to 70%, and the LVDd and LVDs increased significantly, suggesting that the hypertensive heart failure rat model was successfully established.
   4.2 Grouping and administration
   After the model was successfully established, the rats were randomly divided into negative control group, NRG treatment group and captopril treatment group. RhNRG was administered intravenously, with a dose of 6.5 ug/kg, once a day, 5 days of continuous administration and 2 days of drug withdraw period as a treatment cycle. A total of 3 treatment cycles were administered. At the same time, the NRG group was given drinking water by intragastric administration two times a day. Captopril was administered 10 mg/kg by intragastric administration, 2 times a day, continuous administration. NRG excipient was administered by tail vein injection for 3 treatment cycles. The negative control group were given drinking water by intragastric administration and given NRG excipients by tail vein injection.
   4.3 Echocardiography examination
   Before the treatment and at the end of the second and third treatment cycles, echocardiography was examined after ketamine anesthesia to determine the cardiac function changes.
   4.4 Hemodynamic measurement
   At the end of the third treatment cycle, the rats were anesthetized with 3% pentobarbital by intraperitoneal injection. Median incision was made in the neck, the left common carotid artery was isolated and intubated, and the arterial and left ventricular hemodynamic parameters were measured.
5. Experimental results
   Compared with the negative control group, NRG can significantly improve the hemodynamics in hypertensive rats, among which −dp/dt showed statistical difference (respectively −7467.6±715.8 and −5488.1±1340.3, P=0.016); and Captopril could significantly reduce the blood pressure of hypertensive rats (174.5±33.0 vs 216.5±23.2 and 228.0±26.0; p=0.029, p=0.017).
6. Conclusion
   The dose of 6.5 ug/kg of rhNRG was administered to hypertension heart failure rats continuously for 5 days and 2 days of withdrawal period in a treatment cycle. After 2 cycles or 3 cycles of treatment, rhNRG can prevent further left ventricular end diastolic and end systolic volume enlargement, as well as improve hemodynamics, so as to improve the cardiac function of hypertensive heart failure rats. As shown in Table 1, captopril can improve the cardiac function of hypertensive heart failure rats by lowering blood pressure, while rhNRG can improve cardiac function in hypertensive heart failure rats by increasing the dropping rate −dp/dt of left ventricular in isovolumic diastolic period, not by lowering blood pressure.

TABLE 1

Hemodynamic parameters of each group after 3 treatment cycles

| Groups | MAP | −dp/dt |
|---|---|---|
| negative control | 174.7 ± 16.8 | −5488.1 ± 1340.3 |
| NRG | 182.5 ± 18.8 | −7467.6 ± 715.8 |
| captopril | 139.9 ± 24.8 | −5441.2 ± 1007.3 |

Example 2

Study of the Effect of Recombinant Human Neuregulin on Cardiac Function of Heart Failure Patients with Preserved Ejection Fraction To evaluate the effect of recombinant human neuregulin on cardiac function of patients with heart failure with preserved ejection fraction, the preliminary clinical trial was carried out in the Sixth People's Hospital Affiliated to Shanghai Jiao Tong University, which comprises 2 patients in the placebo group and 2 patients in the experiment group.

1 Main inclusion criteria:
1.1 left ventricular ejection fraction (LVEF) ≥50% (two-dimensional echocardiography diagnosis);
1.2 New York heart function (NYHA) II or III level;
1.3 Clear diagnosis of chronic heart failure (including history, symptoms, signs), and clinical symptoms were stable in the last 1 months;
1.4 Patients who received standard therapy for heart failure has reached the target dose or maximum tolerated dose for at least 1 months, or did not change the dose within the last 1 month;
1.5 Understand and sign informed consent form.
2. Trial drugs
Name: recombinant human neuregulin for injection
specifications: 250 g/vial.
Dosage form: lyophilized powder for injection
Route of administration: intravenous drip
Placebo (zero dose):
Name: excipients of lyophilized recombinant human neuregulin
Dosage form: lyophilized powder for injection
Route of administration: intravenous drip
3. Administration route, dosage and course of treatment are shown in Table 2

TABLE 2

Dosage, route and course of treatment

| Dosage | 0 μg/kg/day(Placebo)) | 0.3 μg/kg/day |
|---|---|---|
| Administration route | intravenous drip | |
| course of treatment | 10 hours a day for 10 consecutive days | |
| Dose volume | 50 ml | |

4. Data collection: Mitral valve flow spectrum of two-dimensional echocardiography was detected during the screening period, 11-13 d and 30 d.
5. Results and discussion:

TABLE 3

Numerical changes of IVRT and DT in mitral valve flow spectrum

| | | 8001 (0 ug/kg) | | | 8002 (0 ug/kg) | | | 8003 (0.3 ug/kg) | | | 8004 (0.3 ug/kg) | | |
|---|---|---|---|---|---|---|---|---|---|---|---|---|---|
| | name | Screening period | 11-13 d | 30 d | Screening period | 11-13 d | 30 d | screening period | 11-13 d | 30 d | Screening period | 11-13 d | 30 d |
| parameters | IVRT (ms) | 416.51 | 443.62 | 476.89 | 507.56 | 513.14 | 545.38 | 374.31 | 340.1 | 345 | 621.07 | 609.28 | 499.08 |
| | DT (ms) | 296.76 | 297.89 | 315.56 | 253.85 | 265.81 | 293.96 | 229.08 | 203.7 | 179.5 | 262.28 | 256.15 | 255.14 |

The results of table 3 showed that the IVRT and DT values of patients who administered with placebo were gradually increased, while the IVRT and DT values of patients administered with NRG were significantly decreased, demonstrating a certain degree of improvement of diastolic function.

The examples listed above do not limit the protection scope of the invention. Without departure from the purposes and scope of the present invention, those of ordinary skill in the art may adjust and change the present invention. Therefore, the protection scope of the invention shall be defined by the claims, rather than by specific examples.

What is claimed is:

1. A method for treating heart failure with preserved ejection fraction in a mammal, comprising administering neuregulin to the mammal, wherein the neuregulin is NRG-1.

2. The method of claim 1, wherein the mammal is human.

3. A method for treating heart failure with preserved ejection fraction in a mammal, comprising administering neuregulin to the mammal, wherein the neuregulin comprises the amino acid sequence of SEQ ID NO: 1.

4. The method of claim 3, wherein the mammal is human.

* * * * *